United States Patent [19]

Muller et al.

[11] Patent Number: 4,608,372

[45] Date of Patent: Aug. 26, 1986

[54] PROCESS FOR PREPARING β' FORM OF COPPER 8-HYDROXYQUINOLINE

[75] Inventors: Bernard Muller, St-Germain-en-Laye; René Piat, Bois-Guillaume; Cornelis Rensing, Oissel; Jean-Paul Trajin, Rouen, all of France

[73] Assignee: Hoffmann-La Roche Inc., Nutley, N.J.

[21] Appl. No.: 700,855

[22] Filed: Feb. 12, 1985

Related U.S. Application Data

[60] Division of Ser. No. 572,606, Jan. 20, 1984, Pat. No. 4,517,362, which is a continuation of Ser. No. 393,219, Jun. 28, 1982, abandoned.

[30] Foreign Application Priority Data

Jul. 6, 1981 [FR] France ................................ 81 13249

[51] Int. Cl.$^4$ ..................... C07D 215/30; A01N 55/02
[52] U.S. Cl. .......................................... 514/187; 546/7

[58] Field of Search .............................. 546/7; 514/187

[56] References Cited

U.S. PATENT DOCUMENTS

| 2,689,838 | 9/1954 | Darby | 524/87 |
| 2,756,175 | 7/1956 | Goldstein | 546/7 |

OTHER PUBLICATIONS

Saito et al., Kolloid Zeit. fur. Polymere 212, 156 (1966).

*Primary Examiner*—Mark L. Berch
*Attorney, Agent, or Firm*—Jon S. Saxe; George M. Gould; Patricia A. Coburn

[57] ABSTRACT

A process for the preparation of the β' form of the copper chelate of 8-hydroxyquinoline (copper oxinate), stabilized compositions containing said chelate, fungicidal compositions containing said chelate, and the methods for using said β' form chelate or compositions for combatting fungi are disclosed.

9 Claims, No Drawings

4,608,372

PROCESS FOR PREPARING β' FORM OF COPPER 8-HYDROXYQUINOLINE

This is a division of application Ser. No. 572,606 filed Jan. 20, 1984, now U.S. Pat. No. 4,517,362, which is a continuation of Ser. No. 393,219, filed June 28, 1982, now abandoned.

SUMMARY OF THE INVENTION

The invention relates to a process for preparing the β' form of the copper chelate of 8-hydroxyquinoline. The β' form is prepared by reacting a salt of 8-hydroxyquinoline with a copper (II) salt in water to produce the β form of the chelate, treating the aqueous reaction mixture with base to adjust the pH to about 2–9, isolating the β form and then drying the β form at a temperature between 40°–220° C. to yield the β' form of the chelate.

This invention also relates to stabilized compositions containing the β' form of the copper chelate of 8-hydroxyquinoline, to fungicidal compositions containing said β' form and to methods for the use of the β' form in combatting fungi.

BACKGROUND OF THE INVENTION

It has been known that the chelate of copper (II) with 8-hydroxyquinoline, hereinafter referred to as copper oxinate, possesses biocidal properties and is useful as a fungicide in the treatment of cereal seeds and is also suitable for protecting plants. The advantages of copper oxinate include being non-irritating, possessing very low toxicity, almost zero volatility, high stability and can be prepared without any ecological problems.

The copper oxinate currently marketed possesses valuable activity against fusarium diseases, glume blotch and bunt; however, its activity against leaf stripe of barley is rather low. It is one of the objects of the present invention to find a compund possessing all the advantages of copper oxinate, but also possessing a broad activity spectrum with a high level of efficacy.

It has also been known that copper oxinate is a polymorphous compound, i.e. it has various crystalline forms, see Palenik, Acta. Cryst., 1964, 17(6), 687–695 and Suito, et al., Kolloid-z.z. Polym., 1966, 212(2), 155–161. Seven crystalline forms of copper oxinate have been reported, namely α, α', β, β', β'', γ and γ' forms. The α, α', γ and γ' forms are considered as laboratory curiosities, while the β form is the most stable under normal conditions in which copper oxinate is used.

It has been found that the β' form of copper oxinate, considered to be unstable and to be a transition form between the β form, which is stable under normal conditions, and the β'' form, which is stable at higher temperatures, in fact possesses a broader activity spectrum than the β form and exhibits enhanced efficacy as an antifungal agent.

DETAILED DESCRIPTION OF THE INVENTION

The present invention relates to a process for preparation of the β' form of the copper chelate of 8-hydroxyquinoline (i.e. copper oxinate). The process of the present invention for preparing the β' form of copper oxinate comprises:

(a) reacting a salt of 8-hydroxyquinoline and a copper (II) salt in water;

(b) adding a base until the pH of the reaction is between 2 and 9;

(c) recovering the precipitate of the β form of copper oxinate and (d) drying the β form of copper oxinate at a temperature between about 40° C. and about 220° C. to yield the β' form of copper oxinate.

Copper oxinate in the β' form has a molecular formula $(C_9H_6ON)_2Cu$ and is in the form of a strongly electrostatic, olive-green solid having a filamentous microstructure. The principal X-ray diffraction lines in decimal degrees are: $(2\theta)=7.15; 11.95; 13; 14.7$.

In contrast to the vast majority of organic compounds which can be obtained as pure species by physical purification methods, the physicochemical characteristics of oxine chelates (8-hydroxyquinoline chelates) and particularly the copper (II) oxine chelate are completely determined by the quality of each of the starting materials used, by the composition of the reactants, and by the conditions under which the reaction is carried out, including those relating to washing and drying.

In carrying out the process of this invention, step (a) is conducted in an aqueous phase, preferably an aqueous solution of an oxine salt (i.e. salt of 8-hydroxyquinoline) is reacted with an aqueous solution of a copper (II) salt. It is preferable to carry out this reaction utilizing a slight stoichiometric excess of the oxine salt, for example, less than 5 mol percent.

The preferred oxine salt for this reaction is oxine sulfate; however, other acid addition salts of oxine can be utilized, for example, the nitrate and the phosphate.

The preferred copper (II) salt is copper (II) sulfate; however, other copper (II) salts can be utilized, for example, the nitrate and the phosphate.

The reaction of the oxine salt and the copper (II) salt is carried out at a temperature below 40° C. and, preferably between 0° C. and 20° C., for example, about 10° C.

The acidity resulting from the reaction in step (a) is neutralized in situ by addition of a base. The addition of base is carried out at the same temperature as step (a). Examples of bases which can be employed in the process include ammonia, alkali metal or alkaline earth metal hydroxides, or organic amines. The preferred base is ammonia.

The pH at the end of the reaction is critical because, by adjusting the latter within the range of 2.0–3.5, preferably with the range 2.5–2.8, it is possible to free the reaction mixture not only for the oxine resulting from the neutralization of the excess 8-hydroxyquinoline salt, but also the major part of the oxinates of the other metals which are inevitably present in the reactants, for example Fe, Ni, Ca, and Mg.

The drying step (d) is carried out at temperatures between 40° and 220° C., and preferably between 60° and 160° C. In the latter temperature range, the time period for drying the product will vary between 0.5 second to 120 minutes. If the drying temperature is in the range of 80° to 140° C., the time of drying will be from 0.5 second to 20 minutes. It is understood that the higher the temperature, the shorter the drying time. It should be noted that if the β' form is kept at a high temperature too long, it is converted to the β'' form, which is further converted to the stable β form at ambient temperatures. In fact, over a period of 275 hours at 30° C., 80% of the β'' polymorph is converted to the β form in the presence of water.

The copper oxinate in the β' form prepared according to the process of this invention contains less than 1% of impurities, which makes it a particularly valuable product for the protection of plants.

As noted above, copper oxinate in the $\beta'$ form is readily converted to the $\beta$ form in the presence of water. In the majority of applications, copper oxinate is used in an aqueous medium, for example, in the form of concentrated or dilute aqueous mixtures and, therefore, the use of the $\beta'$ form in such mixtures would lead to rapid conversion to the $\beta$ form.

For practical use of copper oxinate in the $\beta'$ form, it is, therefore, necessary to have available stabilized compositions, for example, wettable powders or aqueous suspensions, which can be stored without conversion to the $\beta$ form and which can be diluted in water at least 24 hours before use, without loss of activity of the product.

Another aspect of the present invention relates to stabilized compositions comprising copper oxinate in the $\beta'$ form, as the active ingredient, and an agent for inhibiting the hydration of the copper oxinate in the $\beta'$ form.

Examples of agents for inhibiting hydration of copper oxinate in the $\beta'$ form include low molecular weight phenoplast-type polycondensates of cresol and formaldehyde, polycondensates of alkylnaphthalenesulfonic acids with formaldehyde, commonly referred to as polyalkylnaphthylmethanesulfonics, and their salts, arenesulfonic acids, for example, benzenesulfonic acid, toluenesulfonic acid, naphthalenesulfonic acid and their salts, polyacrylic acids, their homologoues and their salts, and lignosulfonic acid and lignosulfonates. In addition to their stabilizing properties, the foregoing materials are dispersing surfactants.

In addition to their inherent physicochemical properties, the stabilizers are characterized by the buffering capacity which they impart to the solution, and the presence in their molecules of functional groups, especially OH and/or $NH_2$ and/or $SO_3H$ groups. These functional group are capable of forming a bond of low energy with the copper atom. The following substances are particularly effective hydration inhibitors: 8-hydroxyquinoline-5-sulfonic acid (sulphoxine) and its salts, and halogen substituted sulphoxines, preferably 7-iodo-8-hydroxyquinoline-5-sulfonic acid and its salts.

Other materials which can be employed in the compositions of the present invention include polyvinyl alcohol, alkylcelluloses and hydroxyalkylcelluloses, carboxyalkylcelluloses, polyvinylpyrrolidone, polyacrylamides, carbohydrates, such as starches, hemicelluloses and gums, and polypeptides, in particular casein and caseinates, including powdered milk. These materials impart adhesion to spraying compositions and also have a pronounced stabilizing action and partially inhibit the hydration of the $\beta'$ form.

The concentration of stabilizer in the compositions of this invention depends on the nature of the stabilizer and also varies as a function of the nature of the composition. In general, the stabilizer will be present in the composition in the range of from about 0.1 percent by weight to about 20 percent by weight.

It should be pointed out that copper oxinate is both a brittle and friable material. Therefore, in order to obtain uniform particles having a size which is at the limit of detection of an optical microscope, i.e. in the region of $10^{-4}$ or $10^{-5}$ cm, it is necessary to employ percussion and attrition methods of fragmentation. To obtain the desired particle size, any type of ultramicronization grinder, for example, jet micronizers (air or steam jets) can be used. Preferably, ball grinders or bead mills operating along a horizontal or vertical axis are employed. The procedure is carried out on an aqueous suspension having an oxinate concentration between about 1 and 80% by weight, preferably between 20 and 50% by weight. A colloidal solution containing copper oxinate particles in the appropriate size range can be prepared using beads having a diameter of 1.5 mm as the grinding bodies. During the grinding procedure, all the necessary adjuvants are added to impart stability to the allotrope in question, to assist the micronization or to impart, to the suspension, the optimum characteristics suited to the type of application contemplated.

This invention is also directed to fungicidal compositions useful in combatting fungi of plants and especially seeds. The fungicidal compositions comprise a compatible carrier material and, as the active ingredient, copper oxinate in the $\beta'$ form. These compositions can be, for example, spray liquors, aqueous suspension, and emulsions. They may contain from about 5–20% by weight $\beta'$ copper oxinate and from about 0.5–5% of hydration inhibitor, the rest to 100% being carrier material.

Examples of compatible carrier materials include pulverous materials, such as, for example, kaolin, chalk, bentonite, talc, whiting, magnesium carbonate and siliceous earth. The compositions may also contain wetting agents, inert diluents, solvents, dispersing agents and stabilizers.

Representative examples of the inventive fungicidal compositions are the following:

Compositions for treating the aerial parts of plants, which can be applied in the form of diluent aqueous sprays:

| Ingredient | |
|---|---|
| I. | |
| copper oxinate, $\beta'$ form | 50% |
| sodium polynaphthylmethanesulfonate | 2% |
| sodium lignosulfonate | 3% |
| sulphoxine (8-hydroxyquinoline-5-sulfonic acid) | 1% |
| chalk | 19% |
| kaolin | 25% |
| II. | |
| copper oxinate, $\beta'$ form | 400 g |
| sodium polynaphthylmethanesulfonate | 15 g |
| sodium lignosulfonate | 25 g |
| sulphoxine | 10 g |
| ethylene glycol | 50 g |
| colloidal silica | 25 g |
| silicone anti-foam agent | 2 g |
| polysaccharide | 2 g |
| water, q.s.p. | 1 liter |

The antifungal treatment of seeds may also be combined with protection against insects of the soil as well as bird repellent agents. Lindane is an example of an insecticide which can be employed, and anthraquinone is an example of a bird repellant that may be employed.

An example of a triple composition for treating seeds which can be used in the form of a concentrated aqueous spray is:

| Ingredient | |
|---|---|
| copper oxinate, $\beta'$ form | 15% |
| lindane | 25% |
| anthraquinone | 25% |
| sodium polynaphthylmethanesulfonate | 1% |
| sulphoxine | 0.2% |
| kaolin | 14.8% |
| chalk | 10% |
| polyvinyl alcohol | 5% |

-continued

| Ingredient | |
|---|---|
| red 53-1* | 4% |

*[(4-Hydroxy-1-naphthalenyl)azo]-4'-chloro-5'-methyl-benzene-sulfonic acid barium salt.

The copper oxinate in the $\beta'$ form can also be used in the protection of animal feeds and leather, in the protection of cellulose materials, such as paper pulp, wood, paint, glue and fabrics, and also for the protection of hydrocarbons.

The following Examples illustrate the present invention.

EXAMPLE 1

Preparation of the $\beta$ polymorph: $(C_9H_6ON)_2Cu.2(OH_2)$

A solution prepared from 232.11 g (0.5688 mol and +0.5%) of oxine sulfate and 1,000 ml of water is added, over a period of 30 minutes and with vigorous stirring, to a solution, kept at 10° C., consisting of 142 g (0.5688 mol) of copper sulfate pentahydrate and 1,200 ml of water. The copper oxinate, which has a delicate green color, appears from the introduction of the first drop of reactant, and the polymorphic conversion $\alpha \rightarrow \gamma \rightarrow \beta$ can be followed by examination under a microscope.

The reactants mix without heating being evolved. While maintaining the initial temperature, 85% of the theoretical amount of ammonia (170 ml, $d_{20/4}=0.924$) is introduced dropwise and then, following the pH, the neutralization is continued until the pH is between 2.5 and 2.8($\simeq$10 ml). The temperature is allowed to rise until it reaches ambient temperature, with gentle stirring. The chelate, which is in the form of hexagonal 20$\mu$ lamellae, is filtered off, washed with water (350 ml), drained and left to dry in the open air or using a suitably adjusted fluidized bed apparatus. This yields 250 g of moist product and 219.12 g (yield: 99.4%) of dry product having the following characteristics:

% of $(C_9H_6ON)_2Cu=90.45$; % of $H_2O=9.45$; total content of impurities (other metal oxinates, ammonium sulfate, oxine and water): $\leq 0.40\%$; polymorphic purity by X-ray diffraction: 100%; position of the principal X-ray diffraction lines and in decimal degrees: $(2\theta)=6.95$; 15.75; 16.00.

Before being discarded, the mixture of the mother liquors and the wash liquors (3 liters) is neutralized to pH 7–8 ($\simeq$50 ml) and then allowed to stand for 12 hours. The precipitate, which consists mainly of iron oxinate, that is to say about 0.450 g, cannot easily be removed by filtration, but is more conveniently removed by centrifugation.

EXAMPLE 2

Preparation of the $\beta'$ polymorph: $(C_9H_6ON)_2Cu$

The process of drying the moist $\beta$ polymorph of copper oxinate involves the following two successive steps:

(I) moist $\beta$-oxinate$\rightarrow \beta$-oxinate + moisture;

(II) $\beta$-oxinate$\rightarrow \beta'$-oxinate + 2($OH_2$).

The drying operation (I) can be carried out in the open air or by means of a fluidized bed dryer. In a fluidized bed dryer, the air inlet temperature of which is adjusted to 40° C., the moisture is completely removed in 10 minutes, whereas the degree of conversion in the second step is imperceptible. In fact, to take place in the reasonable period of 10 minutes, the latter requires a temperature of 85° C.

The process can also be carried out by continuously spraying the dry copper oxinate in the $\beta$ form into a steam of hot air, the oxinate being heated to a temperature of 135°–145° C. for a period of the order of a second.

As regards the polymorphic purity, the results commonly obtained are: $\beta$: undetectable; $\beta''$: $\ominus 1\%$. The strongly electrostatic, olive-green solid has a filamentous microstructure under a scanning electron microscope.

Position of the principal X-ray diffraction lines in decimal degrees: $(2\theta)=7.15$; 11.95; 13; 14.7.

EXAMPLE 3

The Example demonstrates the influence of a stabilizer on the preservation of copper oxinate in the $\beta'$ form at ambient temperature and at 60° C. The following compositions were prepared and used in the form of aqueous suspensions containing 5% by weight of copper oxinate in the $\beta'$ form.

Composition A

Copper oxinate in the $\beta'$ form, containing 1% by weight of sulphoxine (8-hydroxyquinoline-5-sulfonic acid in the free form or in the form of the Na salt).

Composition B

Copper oxinate in the $\beta'$ form, containing 10% by weight of Na lignosulfonate.

Composition C

Copper oxinate in the $\beta'$ form, containing 5% by weight of polyoxyether of tridecyl alcohol (unstabilized composition).

| Time | Percentage conversion to the $\beta$ form at ambient temperature | | | | | | | Percentage conversion to the $\beta$ form at 60° C. | | | |
|---|---|---|---|---|---|---|---|---|---|---|---|
| | 0 h 15 m | 1 h | 2 h 30 m | 7 h | 20 h | 90 h | 190 h | 6 months | 0 h 15 m | 1 h | 2 h 30 | 7 h |
| Aqueous suspension containing 5% of copper oxinate in the $\beta'$ form | 4 | 22 | 52 | | 92 | 100 | | | 0 | 100 | | |
| Composition A | 0 | | | | | | 0 | | 0 | 0 | | 0 |
| Composition B | 0 | | | | | | | 0 | | | | |
| Composition C | | | 92 | | | | | | | | | |

These results indicate that the addition of a stabilizer considerably increases the ability of preserving copper oxinate in the $\beta'$ form, in aqueous suspension, whereas the addition of a conventional wetting agent considerably accelerates the conversion to the $\beta$ form.

The following Examples compare the activity of copper oxinate in the $\beta$ and $\beta'$ form in the protection of seeds. The test procedures employed are in accordance with those prescribed by the Commission des Essais Biologiques de la Societe Francaise de Phytiatrie et de Phytopharmacie.

EXAMPLE 4

This Example compares the activity of the $\beta$ and $\beta'$ polymorphs against snow mould, glume blotch and bunt.

The following compositions were prepared:

|  | Percentage by weight |
|---|---|
| Composition D |  |
| Copper oxinate, $\beta$ form | 16.60 |
| Polyethoxy ether of tridecyl alcohol | 0.75 |
| Chalk | 29.20 |
| Kaolin | 53.45 |
| Composition E |  |
| Copper oxinate, $\beta'$ form | 15.00 |
| Polyethoxy ether of tridecyl alcohol | 0.75 |
| Chalk | 29.20 |
| Kaolin | 55.05 |

The compositions were used at a dose equivalent to 30 g/quintal of copper oxinate, expressed as $(C_9H_6NO)_2Cu$. The seeds were treated immediately after preparation of the spraying composition.

The results observed in the protection of the seeds against these diseases are reported in Table I.

TABLE I
ACTIVITY OF $\beta$ AND $\beta'$ COPPER OXINATE ON SNOW MOULD, GLUME BLOTCH AND BUNT

| | Percentage of healthy plantlets Nature of the experiment | | |
|---|---|---|---|
| | SEED CUPS | | OPEN FIELD |
| | Snow[1] mould | Glume[2] blotch | Bunt[3] |
| Disease | Day of counting | | |
| Composition | S + 53 | S + 83 | Harvesting |
| Composition D | 74 | 25 | 92.8 |
| Composition E | 85 | 68.5 | 97 |
| Untreated control | 48 | 6 | 49.3 |

[1]Rye contaminated to the extent of 32% by *Fusarium nivale*
[2]Clement wheat contaminated to the extent of 81% by *Septoria nordorum*
[3]Clement wheat artificially contaminated to the extent of 3°/₀₀ by bunt The activity of $\beta'$ form is much greater than that of the $\beta$ form.

EXAMPLE 5

This Example illustrates the effect of a stabilizer on the activity of the $\beta$ and $\beta'$ polymorphs of copper oxinate against snow mould, glume blotch, bunt and leaf stripe of barley after 24 hours and in the presence of water.

The following compositions were prepared:
Composition G
Copper oxinate, $\beta$ form, at a concentration of 5.55% by weight/volume in water.
Composition H
Copper oxinate, $\beta'$ form, at a concentration of 5% by weight/volume in water.

| Composition I | |
|---|---|
| Copper oxinate, $\beta'$ form | 5 g |
| Na—lignosulfonate | 0.5 g |
| Water, q.s.p. | 100 ml |

The compositions were used at a dose equivalent to 30 g/quintal of copper oxinate, expressed as $(C_9H_6NO)_2Cu$. Unless indicated otherwise, the treatment of the seeds immediately followed the preparation of the spraying mixture. The results observed in the protection of the seeds against these diseases are reported in Table II.

TABLE II
EFFECT OF STABILIZER ON THE ACTIVITY OF $\beta$ AND $\beta'$ COPPER OXINATE AGAINST SNOW MOULD, GLUME BLOTCH, BUNT AND LEAF STRIPE

| | Percentage of healthy plantlets Nature of the experiment | | | |
|---|---|---|---|---|
| | SEED CUPS | | OPEN FIELD | |
| | Snow[1] Mould | Glume[2] Blotch | Bunt[3] | Leaf[4] Stripe |
| Disease | Day of counting | | | |
| Composition | S + 23 | S + 55 | Harvesting | Earing |
| Composition G | 69.3 | 14.7 | 94.9 | 80.4 |
| Composition H | 82 | 81.3 | 99.6 | 97.8 |
| Composition H after 24 h | 75.3 | 40 | .— | — |
| Composition I | 80 | 78.3 | 98.9 | 98.8 |
| Composition I after 24 h | 82.7 | 76.7 | 99.6 | 99.1 |
| Untreated control | 63.3 | 5.3 | 80.6 | 63.6 |

[1]Rye contaminated to the extent of 26% by *Fusarium nivale*
[2]Talent wheat contaminated to the extent of 75% by *Septoria nordorum*
[3]Clement wheat artificially contaminated to the extent of 3°/₀₀ by bunt
[4]Astrix winter barley contaminated to the extent of 56% by *Helminthosporium gramineum*

It is clearly apparent from Table II that the unstabilized aqueous compositions containing copper oxinate in the $\beta'$ form lose a large part of their activity after 24 hours, whereas the stabilized compositions retain a virtually unchanged activity.

EXAMPLE 6

This Example illustrates the efficacy of copper oxinate in the $\beta'$ form in the presence or absence of a stabilizer and in formulations containing other ingredients.

The following compositions were prepared:

|  | Percentage by weight |
|---|---|
| Composition D |  |
| Copper oxinate, $\beta$ form | 16.60 |
| Polyethoxy ether of tridecyl alcohol | 0.75 |
| Chalk | 29.20 |
| Kaolin | 53.45 |
| Composition E |  |
| Copper oxinate, $\beta'$ form | 15.00 |
| Polyethoxy of tridecyl alcohol | 0.75 |
| Chalk | 29.20 |
| Kaolin | 55.05 |
| Composition J |  |
| Copper oxinate, $\beta'$ form | 15.00 |
| Sodium polynaphthylmethanesulfonate | 1.00 |
| Sulphoxine | 0.2 |
| Chalk | 29.2 |
| Kaolin | 54.6 |

The compositions were used at a dose equivalent to 30 g/quintal of copper oxinate, expressed as $(C_9H_6NO)_2Cu$. Unless indicated otherwise, the treatment of the seeds immediately followed the preparation of the spraying mixture.

The results observed in the protection of the seeds against leaf spot are reported in Table III.

TABLE III

EFFECT OF STABILIZER ON THE ACTIVITY OF β AND β' FORM OF COPPER OXINATE ON GLUME BLOTCH

|  | Percentage of healthy plantlets |
|---|---|
| NATURE OF EXPERIMENT | |
| Disease | DISHES |
| Composition | Leaf spot[1] |
| Composition D | 69.8 |
| Composition E after 24 hours | 65.3 |
| Composition J after 24 hours | 91.6 |
| Untreated control | 9.8 |

[1]Talent wheat contaminated to the extent of 90% by *Septoria nodorum*

The results of Table III confirm the efficacy of the stabilizer as regards the β' polymorph.

EXAMPLE 7

This Example illustrates the efficacy of copper oxinate in the β' form in formulations containing other active ingredients, for example, insecticides and bird repellants.

The following compositions were prepared:

|  | Grams/liter |
|---|---|
| Composition K | |
| Copper oxinate, β form | 133.3 |
| Lindane | 200 |
| Anthraquinone | 200 |
| Polyethoxy ether of tridecyl alcohol | 10 |
| Polyethoxy ether of nonylphenol | 15 |
| Red 53-1* | 35 |
| Ethylene glycol | 50 |
| Water, q.s.p. to | 1 liter |
| Composition L | |
| Copper oxinate, β' form | 120 |
| Lindane | 200 |
| Anthraquinone | 200 |
| Red 53-1* | 35 |
| Sulphoxine | 10 |
| Sodium polynaphthylmethanesulfonate | 20 |
| Polyvinyl alcohol | 50 |
| Ethylene glycol | 50 |
| Water, q.s.p. to | 1 liter |

*[(4-Hydroxy-1-naphthalenyl)azo]-4'-chloro-5'methyl-benzene-sulfonic acid barium salt.

The compositions were used at a dose equivalent to 30 g/quintal of copper oxinate, expressed as $(C_9H_6NO)_2Cu$. Unless indicated otherwise, the seeds were treated immediately following preparation of the spray mixture.

The results observed in the protection of the seeds against glume blotch are reported in Table IV.

TABLE IV

EFFECT OF A STABILIZER ON THE ACTIVITY OF β AND β' FORMS OF COPPER OXINATE ON GLUME BLOTCH IN FORMULATIONS CONTAINING OTHER ACTIVE INGREDIENTS

|  | Percentage of healthy plantlets |
|---|---|
| NATURE OF EXPERIMENT | |
| Disease | SEED CUPS |
| Composition | Glume Blotch[1] |
| Composition K | 40.4 |
| Composition L after 24 hours | 81.2 |
| Untreated control | 9.5 |

[1]Talent wheat contaminated to the extent of 90% by *Septoria nodorum*

The results of Table IV confirm the efficacy of the stabilizer as regards the β' polymorph in formulations containing other active ingredients.

We claim:

1. A stabilized composition comprising β' form of copper 8-hydroxyquinoline and a hydration initiator selected from the group consisting of 8-hydroxyquinoline-5-sulfonic acid and salts thereof, halosubstituted 8-hydroxyquinoline-5-sulfonic acid and salts thereof, and of 7-iodo-8-hydroxyquinoline-5-sulfonic acid and its salts.

2. A fungicidal composition which comprises an effective amount of β' form of copper 8-hydroxyquinoline and a hydration inhibitor is selected from the group consisting of 8-hydroxyquinoline-5-sulfonic acid and salts thereof, halosubstituted 8-hydroxyquinoline-5-sulfonic acid and salts thereof, and of 7-iodo-8-hydroxyquinoline-5-sulfonic acid as its salts and an inert carrier material.

3. A method of controlling fungi on plants and seeds comprising treating said plants or seeds with a fungicidally effective amount of the composition of claim 2.

4. The composition of claim 2 comprising from about 5-20% by weight of the β' copper-8-hydroxyquinoline, 0.5-5% by weight of the hydration inhibitor and the rest being carrier material.

5. A stabilized composition comprising β' form of copper 8-hydroxyquinoline and a hydration inhibitor selected from the group consisting of lignosulfonic acid and lignosulfates.

6. The composition of claim 5 wherein the hydration inhibitor is from 0.1 to 20 percent by weight.

7. A fungicidal composition which comprises an effective amount of β' form of copper 8-hydroxyquinoline, a hydration inhibitor selected from the group consisting of lignosulfonic acid and lignosulfonatesfand an inert carrier material.

8. The fungicidal composition of claim 7 comprising from about 5-20% by weight of the β' copper-8-hydroxyquinoline, 0.5-5% by weight of the hydration inhibitor and the rest being carrier material.

9. The composition of claim 1 wherein the hydration inhibitor is from 0.1 to 20 percent by weight.

* * * * *

UNITED STATES PATENT AND TRADEMARK OFFICE
CERTIFICATE OF CORRECTION

PATENT NO. : 4,608,372
DATED : August 26, 1986
INVENTOR(S) : Bernard Muller, Rene Piat, Cornelis Rensing, Jean-Paul Trajin It is certified that error appears in the above-identified patent and that said Letters Patent is hereby corrected as shown below:

In Claim 1, Column 10, Line 19 "initiator" should be
   inhibitor

In Claim 7, Column 10, Line 49 "lignosulfonatesfand" should be
   lignosulfonates Signed and Sealed this Second Day of August, 1988

Attest:

DONALD J. QUIGG

*Attesting Officer*   *Commissioner of Patents and Trademarks*